United States Patent
Baucherel et al.

(10) Patent No.: US 7,019,175 B2
(45) Date of Patent: Mar. 28, 2006

(54) CATALYTIC OXIDATION PROCESS

(75) Inventors: Xavier Baucherel, Delft (NL); Roger Arthur Sheldon, Rijswijk (NL)

(73) Assignee: Imperial Chemical Industries PLC, (GB)

( * ) Notice: Subject to any disclaimer, the term of this patent is extended or adjusted under 35 U.S.C. 154(b) by 0 days.

(21) Appl. No.: 10/480,213

(22) PCT Filed: May 30, 2002

(86) PCT No.: PCT/GB02/02535

§ 371 (c)(1),
(2), (4) Date: Sep. 14, 2004

(87) PCT Pub. No.: WO02/100810

PCT Pub. Date: Dec. 19, 2002

(65) Prior Publication Data

US 2005/0020861 A1    Jan. 27, 2005

(30) Foreign Application Priority Data

Jun. 12, 2001   (GB) .................................. 0114223

(51) Int. Cl.
C07C 45/33 (2006.01)
C07C 35/08 (2006.01)
C07C 27/10 (2006.01)

(52) U.S. Cl. .................. 568/357; 568/375; 568/376; 568/399; 568/836; 568/910

(58) Field of Classification Search ................ 568/357, 568/375, 376, 399, 836, 910
See application file for complete search history.

(56) References Cited

U.S. PATENT DOCUMENTS 5,958,821 A * 9/1999 Ishii et al. .................. 502/167
6,852,893 B1 * 2/2005 Kuhnle et al. ............... 568/314

FOREIGN PATENT DOCUMENTS

| EP | 0824 962 A | 2/1998 |
|---|---|---|
| WO | WO 93 04158 A | 3/1993 |

OTHER PUBLICATIONS

Yautaka Ishii, et al.: "Alkane Oxidation with Molecular Oxygen Using a New Efficient Catalytic System: N-Hydroxyphthalimide (NHPI) Combined with CO(ACAC)N (N=2 OR 3)" Journal of Organic Chemistry, American Chemical Society. Easton, US, vol. 61, No. 14 Jul. 12, 1996 pp. 4520-4526 XP000591064 ISSN: 0022-3263.

E. Schroder, et al.: "Arzeimittelchemie Passage" Arzeneimittelchemie Grundalagen Nerven, Muskeln Und Gewebe, XX, XX, 1976, pp. 30-33, XP002186820 p. 32, the last 3 lines.

H. T. H. Nagasawa, et al.: "Prodrugs of Nitroxyl as Potential Aldehyde Dehydrogenase Inhibitors VIS-À-VIS Vascular Smooth Muscle Relaxants" Journal of Medicinal Chemistry, vol. 38, 1995, pp. 1865-1871, XP002214380.

* cited by examiner

Primary Examiner—Sikarl A. Witherspoon
(74) Attorney, Agent, or Firm—Morgan Lewis & Bockius LLP

(57) ABSTRACT

The invention provides a process for the catalytic oxidation of an alkane, which comprises contacting the alkane with a source of oxygen in the presence of a catalyst comprising a compound of the formula (2) where $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring; Y represents an oxygen atom or a sulfur atom; X represents an oxygen atom or a hydroxyl group; m denotes an integer of 0 to 4; and n denotes an integer of 1 to 3. Compounds in accordance with formula (2) possess good catalytic properties, such that when they are employed in a process in accordance with the present invention, they are capable of activating a source of oxygen and promoting the oxidation of an alkane at mild reaction temperatures.

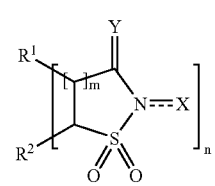

(2)

18 Claims, No Drawings

CATALYTIC OXIDATION PROCESS

FIELD OF THE INVENTION

The present invention relates to a process for the catalytic oxidation of an alkane.

BACKGROUND OF THE INVENTION

The oxidation of saturated hydrocarbons e.g. alkanes, particularly cycloalkanes, with active oxygen such as molecular oxygen or air to produce the corresponding alcohol, ketone and/or acid reaction product(s), has been an area of research activity for many years in view of the utility and environmental benefits of the reaction to the chemical industry.

The oxidation of cycloalkanes in particular has proved to be a difficult reaction to carry out, typically requiring harsh reaction conditions and/or resulting in poor conversion of the starting material and/or poor selectivities of desired reaction products. For example, it is know from the literature to oxidise an alkane such as cyclohexane, with air, in the presence of a cobalt catalyst. The reaction however requires conditions of high temperature and pressure to activate oxygen. Further, under these conditions, in order to obtain a reasonable selectivity of the products, the conversion or transformation rate of the starting material has to be suppressed below about 10%. An alternative reaction involves carrying out the autoxidation of a macrocyclic alkane e.g. cyclododecane, with molecular oxygen in the presence of a stoichiometric amount of boric acid, metaboric acid or boric anhydride to produce alkyl borate reaction products. These reaction products are hydrolysed in a later step, to provide the corresponding alcohol and boric acid. The conversion of the macrocyclic alkane starting material is still however generally poor, and therefore the overall yields of the desired reaction products are typically low.

A further catalytic system has been described in EP-A-824,962. This document describes a catalytic oxidation system comprising an N-hydroxyphthalimide compound of formula (1) below and a co-catalyst, which system is described as promoting the efficient oxidation of a substrate under relatively mild conditions. For example, the oxidation of cyclohexane using N-hydroxyphthalimide and a manganese (II) co-catalyst is described as proceeding at atmospheric pressure (1 atm) and a temperature of 100° C. to produce a carboxylic acid, with no formation of ketone and alcohol intermediates being observed.

Formula 1

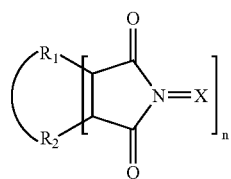

A further reported reaction was the oxidation of cyclododecane in the presence of N-hydroxyphthalimide, a cobalt (II) co-catalyst and oxygen at atmospheric pressure and a reaction temperature of 100° C.

Although the catalytic oxidation system proposed in EP-A-824,962 goes some way to enabling the catalytic oxidation reaction of alkanes, particularly cycloalkanes, to be carried out under comparatively mild to moderate conditions compared with earlier reported methods, there is still a need for new catalysts which demonstrate improved reactivity, being effective at conditions of even lower temperature compared with the catalysts of the prior art.

Additionally, or alternatively, typically the new catalysts will demonstrate improved selectivities and/or product conversion against known catalysts.

STATEMENT OF THE INVENTION

In one aspect, the invention provides a process for the catalytic oxidation of an alkane, which comprises contacting the alkane with a source of oxygen in the presence of a catalyst comprising a compound of the following formula:

Formula 2

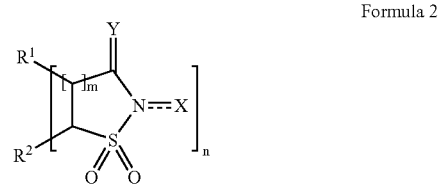

where $R^1$ and $R^2$ independently represent a hydrogen atom, a halogen atom, an Alkyl group, an aryl group, a cycloalkyl group, a hydroxy group, an alkoxy group, a carboxyl group, an alkoxycarbonyl group, or arm acyl group, or $R^1$ and $R^2$ may together form a double bond or an aromatic or non-aromatic ring; Y represents an oxygen atom or a sulfur atom; X represents an oxygen atom or a hydroxyl group; m denotes an integer of 0 to 4; and n denotes an integer of 1 to 3.

The term "selectivity" as used herein means the relative proportions of each of the reaction products, i.e. typically of the ketone and alcohol, on a mole basis expressed as a percentage of the number of moles of converted starting material for a particular catalytic oxidation reaction

Alkane

The catalytic oxidation of an alkane provides a corresponding alcohol, ketone, or carboxylic acid reaction product, or mixtures thereof.

Preferably, the alkane is a cycloalkane, where the tern "cycloalkane" as used herein should be understood to include macrocyclic cycloalkanes having a carbon ring of 8 or more and up to 25 members and simple cycloalkanes having a carbon ring of less than 8 members but greater than 4 members e.g. cyclopentane, cyclohexane.

Typically, the cycloalkane is a C5 to C20 membered ring

Suitable cycloalkanes for use in the process described herein include, for example, cyclopentane, cyclohexane, cycloheptane, cyclooctane, cyclononane, cyclodecane, cycloundecane, cyclododecane, cyclotridecane, cyclotetradecane, cyclopentadecane, cyclohexadecane, cyclooctadecane, cyclononadecane, cycloicosane, cyclodocosane or cyclotetracosane.

Conveniently, the cycloalkane may be substituted or unsubstituted. Preferably, the cycloalkane is unsubstituted However, suitable substituted cycloalkanes include for example cycloalkanes each having a hydroxyl group (e.g., cyclohexanol, cyclooctanol, cyclodecanol, cycloundecanol, cyclododecanol, cyclotetradecanol cycloicosanol), cycloalkanes each having an oxo group (e.g., cyclopentanone, cyclohexanone, methylcyclohexanone, dimethylcyclohexanone, cyclohexadione, cyclopentanone, cyclooctanone, cyclooctadione, cyclononanone, cyclodecanone, cycloundecanone, cyclododecanone, cyclotetradecanone, cyclooctadecanone, cycloiscosanone), cycloalkanes each having an alkyl group (e.g. methylcyclohexane, 1,2-dimethylcyclohexane, isopropylcyclohexane, methylcyclooctane).

Further suitable alkanes for use in the process in accordance with the present invention are linear alkanes which may be unsubstituted or substituted e.g. benzylic alkanes such as ethylbenzene, or allylic alkanes.

Compounds of Formula (2)

Compounds of formula (2) are cyclic, where m typically denotes an integer of 0 to 4, and is preferably 0.

In the compounds represented by formula (2), $R^1$ and $R^2$ may be a halogen atom such as, for example, an iodine, bromine, chlorine or fluorine atom. The alkyl group may be a straight chain or branched chain of 1 to 10 carbon atoms, which may be substituted with one or more substituents or m-Lay be unsubstituted. Examples of suitable alkyl groups include, for example, methyl, ethyl, propyl, isopropyl, butyl, isobutyl, sec-butyl, t-butyl, pentyl, hexyl, heptyl, octyl, nonyl or decyl groups. Preferably, the alkyl group is an alkyl group of 1 to 6 carbon atoms, and more preferably is a lower alkyl group of 1 to 4 carbon atoms.

Suitable aryl groups include, for example, a phenyl group or a naphthyl group. Examples of suitable cycloalkyl groups include cyclopentyl, cyclohexyl, and cyclooctyl groups. Suitable alkoxy groups include, for example, methoxy, ethoxy, propoxy, isopropoxy, butoxy, isobutoxy, t-butoxy, pentyloxy, hexyloxy, and other alkoxy groups each having 1 to 10 carbon atoms. Among them, alkoxy groups having 1 to 6 carbon atoms, in particular lower alkoxy groups having 1 to 4 carbon atoms are desirable.

Examples of suitable alkoxycarbonyl groups include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups having 1 to 10 carbon atoms in the alkoxy moiety. A preferred alkoxycarbonyl group includes 1 to 6 carbon atoms in the alkoxy moiety, among which lower alkoxycarbonyl groups having 1 to 4 carbon atoms in the alkoxy moiety are typically desirable.

Examples of suitable acyl groups include, for example, formyl, acetyl, propionyl, butyryl, isobutyryl, valeryl, isovaleryl, pivaloyl, and other acyl groups having 1 to 6 carbon atoms.

$R^1$ and $R^2$ may either be the same or different.

In the compounds represented by formula (2), $R^1$ and $R^2$ may together form a double bond, or an aromatic or non-aromatic ring. A preferred aromatic or non-aromatic ring may be a C5 to C12 membered ring, in particular a C6 to C10 membered ring and more particularly a C6 membered ring. Suitable rings may include, a heterocyclic ring or a condensed heterocyclic ring, a hydrocarbon ring such as non-aromatic alicyclic rings (e.g. a cyclohexane ring or other cycloalkane rings which may optionally have one or more substituents, a cyclohexene ring or other cycloalkene rings which may optionally be substituted), non-aromatic bridged (cross-linked) rings (e.g. a 5-norbornene ring or other optionally substituted bridged hydrocarbon rings), aromatic rings such as a benzene ring, naphthalene ring or other aromatic rings which may optionally be substituted. The ring may practically comprise an aromatic ring.

The $R^1$ and $R^2$ substituents of a compound of formula (2) are not thought to be involved in the catalytic oxidation of an alkane. This is because the reaction mechanism for the N-hydroxyphthalimide (NHPI) catalyst of EP-A-824,962, illustrated, for example, in Ishii et al., *Chem. Commun.*, 2000, 163–164, shows that the hydrogen atom of the hydroxyl group on NHPI is abstracted by oxygen or a co-catalyst/oxygen complex to form the PINO radical intermediate, followed by addition of a hydrogen atom abstracted from the alkane to the PINO radical, to reform NHPI. Thus, $R^1$ and $R^2$ do not participate in the activation of oxygen, and as such, the nature of these groups is irrelevant for the mechanism of action of compounds of formula (2) useful herein. Consequently, $R^1$ and $R^2$ may be selected from a broad range of substituents as described above.

Suitable catalysts for use herein include compounds shown by the following formulae: (2a) to (2g).

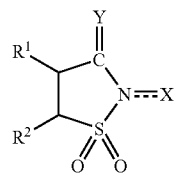

Formula (2a)

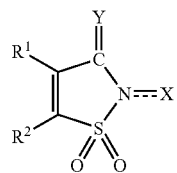

Formula (2b)

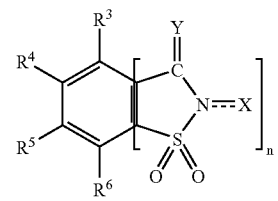

Formula (2c)

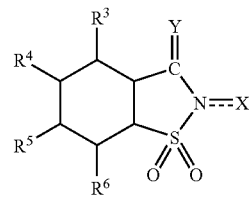

Formula (2d)

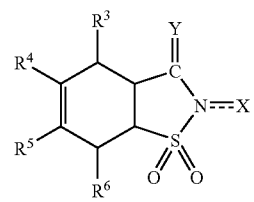

Formula (2e)

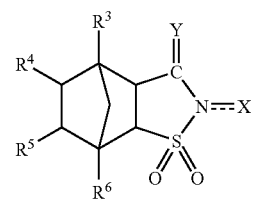

Formula (2f)

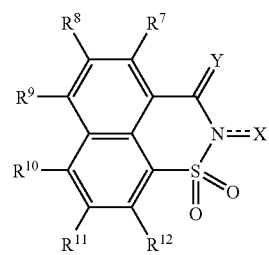

Formula (2g)

wherein $R^3$, $R^4$, $R^5$, $R^6$, $R^7$, $R^8$, $R^9$, $R^{10}$, $R^{11}$ and $R^{12}$, independently represent a hydrogen atom, an alkyl group, a hydroxyl group, an alkoxy group, a carboxyl group, an alkoxycarbonyl group, an acyl group, a nitro group, a cyano group, an amino group or a halogen atom; the bond between the nitrogen atom "N" and X denotes a single bond or a double bond; and where $R^1$ and $R^2$ have the same meanings as described above, and n, X and Y have the same meanings as described below.

With regard to the substituents $R^3$, $R^4$, $R^5$, $R^6$, $R^7$, $R^8$, $R^9$, $R^{10}$, $R^{11}$ and $R^{12}$, the alkyl group may be as described above, and is preferably an alkyl group having 1 to 6 carbon atoms. The alkoxy group may be as described above, particularly a lower alkoxy group having 1 to 4 carbon atoms. Examples of suitable alkoxycarbonyl groups include those mentioned above, especially lower alkoxycarbonyl groups having 1 to 4 carbon atoms in the alkoxy moiety. As the acyl group, there may be mentioned the acyl groups described above, in particular acyl groups having 1 to 6 carbon atoms. Examples of suitable halogen atoms include fluorine, chlorine and bromine atoms. The substituents $R^3$, $R^4$, $R^5$, $R^6$, $R^7$, $R^8$, $R^9$, $R^{10}$, $R^{11}$ land $R^{12}$, may practically, each independently be hydrogen atoms, lower alkyl groups having 1 to 4 carbon atoms, carboxyl groups, nitro groups or halogen atoms.

Y represents an oxygen atom or a sulfur atom and is preferably an oxygen atom.

X represents an oxygen atom or a hydroxyl group and is preferably a hydroxyl group. As such, preferably the bond between the nitrogen atom N and X is a single bond.

Further, n denotes an integer of 1 to 3, preferably 1 or 2, and is more preferably 1.

One or more compounds represented by formula (2) can be used to catalyse an oxidation reaction.

In a preferred embodiment herein, $R^1$ and $R^2$ together form an aromatic, unsubstituted, C6 membered ring i.e. where $R^3$, $R^4$, $R^5$ and $R^6$ of formula (2c) are each independently a hydrogen atom; n is 1; Y is O and X is a hydroxyl group. In this particular embodiment, the preferred catalyst is therefore N-hydroxysaccharin (also known as "2-hydroxy-1,2-benzisothiazol-3(2H)-one 1,1-dioxide", which may be referred to herein for simplicity and brevity as "NHS") and which may be prepared according to the method described in Nagasawa et al (*J. Med. Chem.*, 1995, 38, 1865–1871).

Generally, compounds of formula (2) may be prepared from a sulfo anhydride compound by an imidation process as would be known to those skilled in the art.

Compounds of formula (2) have been found to possess good catalytic properties and are capable of activating a source of oxygen and promoting oxidation of an alkane at even milder reaction temperatures than has been demonstrated with the N-hydroxyphthalimide catalysts of EP-A-824,962.

Generally, the amount of a compound of formula (2) employed in the catalytic oxidation reaction of an alkane is selected from a broad range of about 0.001 to 1 mole (0.01 to 100 mole %), preferably about 0.001 to 0.5 mole (0.1 to 50 mole %), more preferably about 0.01 to 0.30 mole, and even more preferably about 0.01 to 0.25 mole, per 1 mole of alkane.

The catalyst comprising a compound of formula (2) may be whichever of a homogeneous system or a heterogeneous system. The oxidation catalyst or oxidation catalytic system may also be a solid catalyst comprising a catalytic component supported on a support or carrier. As the support, use can be practically made of activated carbon, zeolite, silica, silica-alumina, bentonite, or other porous supports. In the solid catalyst, a supporting amount of the catalytic component may be such that a relative ratio of a compound of formula (2) to 100 parts by weight of the support is about 0.1 to 50 parts by weight, preferably about 0.5 to 30 parts by weight and more preferably about 1 to 20 parts by weight.

In the presence of a source of oxygen and a catalyst comprising a compound of formula (2) described herein, an alkane undergoes a catalytic oxidation reaction to conveniently provide reaction products including a ketone, particularly a monoketone, in moderate to high yield. This reaction occurs even when the alkane is a macrocyclic cycloalkane having a C8 or more membered ring, particularly a C9 or more membered ring (e.g., a C10 to C25 membered cycloalkane), which alkanes generally have little activity to oxidation. Specifically, in a process described herein, a cycloalkane can be oxidised in mild conditions with high conversion and selectivity to provide a ketone, particularly, a macrocyclic monoketone, e.g. cycloalkanone. Such a ketone may be a useful precursor, for example, in the preparation of a long chain dicarboxylic acid which may be employed as a raw material for polyester, polyamide or a plasticizer.

Co-Catalyst

The catalyst utilised in the oxidation reaction of an alkane, may optionally comprise, in addition to a compound of formula (2), a co-catalyst, or mixtures thereof.

Suitable co-catalysts for use herein conveniently have oxidising properties. Typically, the co-catalysts comprise a metal, metal complex, or metal compound, where the metal may be a transition metal or an alkaline earth metal. Alternatively, the co-catalyst may be a compound comprising an element such as boron or other compounds containing a Group 3B element e.g. aluminium Al of the Periodic Table of Elements.

Examples of suitable alkaline earth metals include magnesium Mg, calcium Ca, strontium Sr, and barium Ba from the Group 2A elements of the Periodic Table of Elements.

As suitable examples of transition metals, there may be mentioned, for example, Group 3A elements of the Periodic Table of Elements (e.g., scandium Sc, yttrium Y, and lanthanum La, cerium Ce, samarium Sm and other lanthanoid elements, actinium Ac and other actinoid elements), Group 4A elements of the Period Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2B elements (e.g. zinc Zn, cadmium Cd).

In particular, high oxidising activities may be demonstrated when a compound of formula (2) is used in combination with a compound containing Ti, Zr or other Group 4A elements, V or other Group 5A elements, Cr, Mo, W or other Group 6A elements, Mn, Tc, Re or other Group 7A elements, Fe, Ru, Co, Rh, Ni or other Group 8 elements, or Cu or other Group 1B elements.

As the boron compound, there may be mentioned for example a boron hydride (e.g. diborane, tetraborane, pentaborane, decaborane), a boric acid (e.g., orthoboric acid, metaboric acid, tetraboric acid), a borate (e.g. nickel borate, magnesium borate, manganese borate), $B_2O_3$ and other boron oxides, borazane, borazene, borazine, boron amide, boron imide, and other nitrogen-containing boron compounds, $BF_3$, $BCl_3$, tetrafluoroborate, and other halides, esters of boric acid (e.g., methyl borate, phenyl borate) and so on A preferred boron compound for use herein includes boron hydrides, orthoboric acid, and other boric acids or salts thereof among which a boric acid can preferably be employed. These co-catalysts may be employed singly or in combination.

Suitable metal compounds for the co-catalyst may practically include a metal hydroxide, a metal oxide including a double oxide or an oxygen acid salt, a metal halide, an organic acid salt, an inorganic acid salt, a co-ordinate compound (a metal complex), or a polyacid, e.g. a heteropolyacid or an isopolyacid, or its salt which contains a metal element.

Suitable metal hydroxides for use herein typically include for example $Mn(OH)_2$, $MnO(OH)$, $Fe(OH)_2$ and $Fe(OH)_3$.

Examples of suitable metal oxides are as described in EP-A-824,962, which is incorporated herein by reference. As examples of the double oxide or oxygen acid salt there may be mentioned, for example, $MnAl_2O_4$, $MnTiO_3$, $LaMnO_3$, $K_2Mn_2O_5$, $CaO.xMnO_2$ (x=0.5, 1, 2, 3, 5), and the further manganese salts exemplified in EP-A-824,962.

Examples of suitable metal halides are as described in EP-A-824,962 and include for instance $FeCl_3$ and $CuCl_2$, and complex halides such as $M^1MnCl_3$, $M^1_2MnCl_5$, $M^1_2MnCl_6$, wherein $M^1$ represents a monovalent metal Examples of suitable organic acid salts include cobalt acetate, manganese acetate, cobalt propionate, manganese propionate, cobalt naphthenate, manganese naphthenate, cobalt stearate, manganese stearate, and other salts with a $C_{2-20}$ fatty acid, manganese thiocyanate, and corresponding salts of Ce, Ti, Zr, V, Cr, Mo, Fe, Ru, Ni, Pd, Cu and Zn.

Examples of suitable inorganic acid salts include, for instance, nitrate, sulfate, phosphate and carbonate salts of Co, Fe, Mn, Ni and Cu (e.g., cobalt sulfate, iron phosphate, manganese carbonate, iron perchlorate).

A co-ordinate compound (or complex) suitable for use herein typically comprises a transition metal element and one or more ligands.

Examples of suitable ligands which may constitute the complex include a hydroxyl group, methoxy, ethoxy, propoxy, butoxy and other alkoxy groups, acetyl, propionyl and other acyl groups, methoxycarbonyl (acetato), ethoxycarbonyl and other alkoxycarbonyl groups, acetylacetonato (acac), a cyclopentadienyl group, a halogen atom, CO, CN and derivatives thereof, oxygen atom, $H_2O$, $NH_3$ (amine), NO, $NO_2$ (nitro), $NO_3$ (nitrato), ethylenediamine, diethylenetriamine pyridine, phenanthroline and other nitrogen-containing compounds. In the complexes or complex salts, the same or different ligands may be co-ordinated singly or in combination to the transition metal.

The ligand is practically, for example, an acyl group, an alkoxycarbonyl group, acetylacetonato, a halogen atom, CN and derivatives thereof, and $H_2O$ (aquo).

Examples of suitable complexes for use herein are described in EP-A-824,962 and include for instance acetylacetonato complexes (e.g., acetylacetonato complexes of Fe, Co or Cu) and acetyl complexes (e.g. cobalt acetate and copper acetate).

The polyacid (isopolyacid or heteropolyacid) typically comprises at least one member selected from the Group 5A elements or Group 6A elements of the Periodic Table of Elements such as V (vanadic acid), Mo (molybdic acid) or W (tungstic acid). However, there is no particular restriction on the type of metal element employed and it may be any of the metals illustrated and described in EP-A-824,962. As illustrative examples of a heteropolyacid, there may be mentioned cobaltmolybdate, cobalttungstate, molybdenumtungstate, manganesemolybdate manganesetungstate, manganesemolybdenumtungstate, vanadomolybdophosphate, manganesevanadiummolybdate, vanadiummolybdenum (phosphovanadomolybdate) or phosphovandomolybdic acid, and manganesevanodomolybdophosphate. In the co-catalyst constituting the oxidation catalytic system of the present invention, a preferred polyacid is an isopolyacid.

The characteristic functions of a particular co-catalyst will depend upon the species of co-catalyst and are as described in EP-A-824,962, which is incorporated by reference herein.

An effective co-catalyst for use herein when the alkane is a cycloalkane, is typically a compound containing at least a Group 8 element (e.g. Co) of the Periodic Table of Elements. A further effective co-catalyst may comprise a combination of a compound containing a Group 7A element (e.g., Mn) of the Periodic Table of Elements with a compound containing a Group 8 element (e.g. Fe) of the Periodic Table of Elements.

A further effective co-catalyst for use herein is a divalent transition metal compound, i.e. a divalent cobalt compound e.g. acetylacetonatocobalt $Co(acac)_2$ or a divalent manganese compound, which typically ensures production of a cycloalkanone from a corresponding cycloalkane with significantly improved selectivity and yield. Use of such a co-catalyst may also inhibit the by-production of a diketone.

Preferred co-catalysts useful herein may be selected from one or more of $Co(acac)_2$, $Co(OAc)_2.4H_2O$, $Cu(OAc)_2.4H_2O$, $Cu(acac)_2$, $Ru(CH_3CN)_4Cl_2$, $Fe(acac)_3$ or $Co(acac)_3$.

The ratio of co-catalyst (a co-oxidising agent), when present, to alkane can be liberally selected from a range not interfering with the activity and selectivity, and is generally about 0.0001 mole (0.1 mole %) to 0.7 mole (70 mole %), preferably about 0.0001 to 0.5 mole, and more preferably about 0.001 to 0.3 mole relative to one mole of alkane. The co-catalyst is practically used in a ratio of 0.0005 to 0.1 mole (preferably about 0.005 to 0.1 mole) per one mole of alkane.

The relative ratio of co-catalyst when present to a compound of formula (2) may be selected from a range not interfering with the reaction rate and selectivity, and is generally for example, about 0.001 to 10 moles, preferably about 0.005 to 5 moles, and more preferably about 0.01 to 3 moles relative to one mole of a compound of formula (2). The co-catalyst may practically be employed in an amount of 0.01 to 5 moles (particularly 0.001 to 1 mole) relative to one mole of a compound of formula (2).

Incidentally, the activity of a compound of formula (2) may sometimes deteriorate with an increasing ratio of the co-catalyst Therefore, for retaining a high activity of the oxidation catalytic system, a preferred ratio of the co-catalyst, relative to one mole of a compound of formula (2), is not less than an effective amount and not greater than 0.1 mole (e.g., about 0.001 to 0.1 mole, preferably about 0.005 to 0.08 mole, and more preferably about 0.01 to 0.07 mole).

If the cocatalyst is supported on a support, typically the ratio of the co-catalyst supported on the support is about 0.1 to 30 parts by weight, preferably about 0.5 to 25 parts by weight and more preferably about 1 to 20 parts by weight, relative to 100 parts by weight of the support When a polyacid (an isopolyacid or a heteropolyacid) or its salt is used as the co-catalyst, the ratio of the polyacid, relative to 100 parts by weight of an alkane is typically about 0.1 to 25 parts by weight, preferably about 0.5 to 10 parts by weight, and more preferably about 1 to 5 parts by weight Oxidation Reaction The oxygen source employed in the catalytic oxidation of an alkane may be active oxygen i.e. hydrogen peroxide, perborate, peracid, percarbonate, molecular oxygen, but typically it is, economically advantageous to employ molecular oxygen Generally, there are no restrictions on the type of molecular oxygen which may be usefully employed and use may be made of whichever of pure oxygen gas or oxygen diluted with an inert gas such as nitrogen, helium, argon or carbon dioxide gas. Air may also be employed from the viewpoint of its handling properties and safety. Preferably, the reaction is carried, out in an atmosphere of molecular oxygen such as air or oxygen gas.

The amount of oxygen which may be used in the catalytic oxidation process described herein is generally in the range 0.5 mole or more (e.g., 1 mole or more), preferably about 1 to 100 moles, and more preferably about 2 to 50 moles relative to 1 mole of the alkane. For practical purposes oxygen is generally used in an excess amount-relative to the number of moles of alkane.

The catalytic oxidation reaction is generally carried out in a solvent, typically an inert organic solvent. Suitable organic solvents include, for example, acetic acid, and other organic carboxylic acids or hydroxycarboxylic acids, acetonitrile, benzene and other aromatic hydrocarbons including trifluorotoluene, and mixtures of these solvents. Preferred organic solvents for use herein include acetic acid and trifluorotoluene. Alternatively, the alkane may be employed as the reaction solvent, if used in excess amount.

Optionally, the reaction may be carried out in the presence of a protic acid which facilitates smooth oxidation of the alkane. Further, carrying out the reaction in the presence of such an acid generally-provides the desired oxidised compound with high selectivity in a high yield. The protic acid may also be employed as the reaction solvent. Examples of suitable protic acids include organic acids such as formic acid, acetic acid, propionic acid and other organic carboxylic acids, oxalic acid, succinic acid, tartaric acid and other hydroxycarboxylic acids, methanesulfonic acid, ethanesulfonic acid and other alkylsulfonic acids, benzenesulfonic acid, p-toluenesulfonic acid and other arylsulfonic acids, and inorganic acids such as hydrochloric acid, sulfuric acid, nitric acid, phosphoric acid.

The process in accordance with the present invention is characterised in that typically, the oxidation reaction smoothly proceeds to the desired reaction product(s) even in comparatively mild conditions at ambient temperatures. Generally, the catalytic oxidation reaction is carried out at a temperature in the range of, for instance, from about 0 to 300° C., preferably from about 20 to 250° C., more preferably from about 20 to 150° C., and practically from about 20 to about 100° C. As described above, the oxidation reaction can smoothly proceed even at a comparatively low temperatures such as room temperature.

The reaction may be carried out at ambient pressure (atmospheric pressure) or under increased pressure. Preferably, the reaction is carried out at atmospheric pressure. When the reaction is conducted under increased pressure, the pressure is, usually, about 1.5 to 100 atm, preferably about 2 to 70 atm, and more preferably about 5 to 50 atm. A reaction time can be liberally chosen within a range of about 30 minutes to 48 hours, preferably about 1 to 36 hours, and more preferably about 2 to 24 hours, according to the reaction temperature and pressure.

The reaction may be effected in conventional manner such as in a batch system, semi-batch system or continuous system, in the presence of active oxygen, typically, molecular oxygen or under the flow of molecular oxygen. After completion of the reaction, a reaction product can easily be isolated and purified via one or more conventional procedures, such as filtration, condensation, distillation, extraction, crystallisation, recrystallisation, column chromatography, or other isolation means.

Alternatively, if an oxidation reaction product contains a hydrophilic group, it may be isolated from the reaction mixture according to the process described in EP-A-825,165, where the utilisation of an aqueous solvent and a non water-soluble solvent in the reaction work up, effects the distribution of hydrophilic oxidation reaction products into the aqueous solvent layer and the catalyst into a non-water soluble solvent layer. This process thereby conveniently enables efficient isolation of some oxidation reaction products and recovery of the catalyst, so that the latter may be reused in further reactions.

The invention is illustrated by way of the following non-limiting examples in which:

In Examples 2 to 6, the conversions and selectivities reported are determined by gas chromatography (GC) using 1,2,4-trichlorobenzene as an internal standard. In each of these examples, 200 mg of 1,2,4-trichlorobenzene was added to each reaction mixture as standard.

GC Conditions utilised for analyses in the following Examples:

| | |
|---|---|
| GC: | Varian Star 3600 equipped with an autosampler (Varian 8200) |
| Column: | CP Sil 5 CB 50 m × 0.53 mm; o.d. 0.70 mm; df 1.00 µm; ratio 133 |
| Carrier Gas: | Nitrogen |
| Temperature Programme: | |
| Injector: | 70° C. for 0.1 minute, then 150° C./min to 300° C., hold 0.5 minutes at 300° C. |
| Detector: | 300° C. |
| Oven: | 70° C. for 2 minutes, then 10° C./min to 300° C., hold 10 minutes at 300° C. |

EXAMPLE 1

Preparation of N-hydroxysaccharin

N-hydroxysaccharin was prepared according to the following reaction scheme:

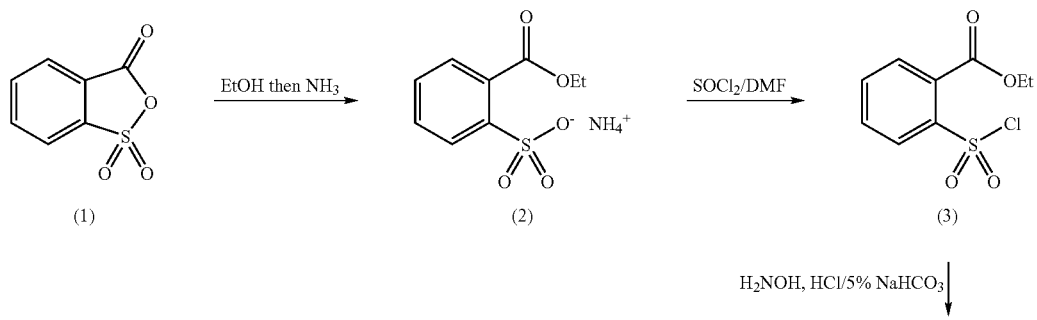

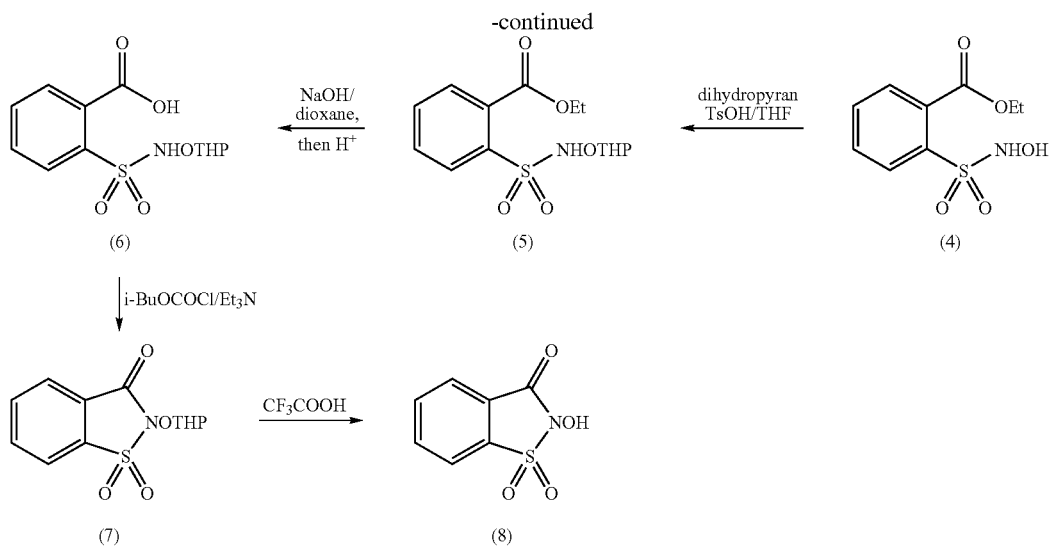

Synthesis of Ammonium 2-(Ethoxycarbonyl)benzenesulfonate (2)

2-Sulfobenzoic anhydride (1; 50.2 g, 0.270 mol) in 160 ml of absolute ethanol was stirred overnight. After the addition of 60 ml of 7N methanolic ammonia, the mixture was stirred for a further 2 hours and the resulting thick white reaction mixture was clarified by addition of 160 ml of methanol. The solution was diluted with ether (1.1 L) until no more solids precipitated, and the product was collected by filtration and air-dried overnight to give 60.6 g (91% yield) of (2).
$^1$H NMR (D$_2$O) δ 1.35 (t, 3H, CH$_3$), 4.40 (q, 2H, CH$_2$), 7.56 (m, 3H, Ar—H), 7.90 (m, 1H, Ar—H).

This product was used in the next step without further purification.

Synthesis of Ethyl 2-(Chlorosulfonyl)benzoate (3)

Compound 2 obtained above (10.0 g, 0.040 mol) was suspended in dimethyl formamide (7 ml), and thionyl chloride (54 ml) was added dropwise. The reaction mixture was heated under reflux overnight and then cooled in an ice bath and carefully added to crushed ice (about 600 g). The cold mixture was immediately extracted with dichloromethane (3×70 ml). The organic layer was washed with 5% NaHCO$_3$ (100 ml) and then water (100 ml) and dried over MgSO$_4$. Evaporation of the solvent gave a light clear oil (10 g quantitative yield). The product was used in the next step without any further purification.
Rf: hexane/EtOAc (3/1) (silica chromagel; 60F$_{254}$ available from Merck): 0.35 $^1$H NMR (CDCl$_3$): δ 1.43 (t, 3H, CH$_3$), 4.46 (q, 2H, OCH$_2$), 7.72–7.78 (m, 3H, H$_{arom}$), 8.16 (m, 1H, H$_{arom}$) $^{13}$C NMR (CDCl$_3$): δ 13.8 (CH$_3$), 62.9 (CH$_2$), 129.0, 130.2, 131.4, 132.7, 135.2 and 141.5 (6 C$_{arom}$), 165.9 (C=O)

Synthesis of Ethyl 2-[(N–Hydroxyamino)sulfonyl]benzoate (4)

To a solution of ethyl 2-(chlorosulfonyl)benzoate (3; 10.0 g, 40.2 mmol) in tetrahydrofuran (130 ml) was added a solution of hydroxylamine-hydrochloride (5.60 g, 80.1 mmol) in water (37 ml). The mixture was cooled in an ethanol-dry ice bath at −10 to −15° C., and 10% NaHCO$_3$ (135 ml, 160.5 mmol) was added dropwise with stirring over a period of 1 hour.

After stirring for a further hour, two layers separated. The aqueous bottom layer was extracted twice with dichloromethane (1×75 ml and 1×40 ml), and the combined organic extracts were added to the THF top layer. The combined solution (cloudy) was washed with water (75 ml), and the organic layer was dried (MgSO$_4$) and evaporated to give compound (4) as a clear yellow solid (6.50 g, 66% yield). The product was used in the next step without any further purification.
$^1$H NMR (CDCl$_3$): δ 1.42 (t, 3H, CH$_3$), 4.45 (q, 2H, OCH$_2$), 7.67–7.71 (m, 2H, H$_{arom}$), 7.85–7.89 (1H, H$_{arom}$) 8.17–8.2 (m, 1H, H$_{arom}$), 8.6 (s, 1H, NH) $^{13}$C NMR (CDCl$_3$): δ 14.0 (CH$_3$), 63.0 (CH$_2$), 130.9, 131.5, 131.6, 132.7, 133.6 and 135.3 (6 C$_{arom}$), 167.5 (C=O)

Synthesis of Ethyl 2-[[N-Tetrahydropyranyloxy) amino]sulfonyl]-benzoate (5)

To a solution of (4) (6.50 g, 26.5 mmol) in dichloromethane (125 ml) was added dihydropyran (4.80 ml, 52.3 mmol) and p-toluenesulfonic acid monohydrate (100 mg). The reaction mixture was stirred at room temperature for 1 hour, and the dark reaction mixture was evaporated to give a dark coloured oil. The oil was purified by flash column chromatography on Kieselgel 6 using EtOAc:hexane (1:6) as the eluting solvent to give 8.70 g of (5) as a light yellow oil (quantitative yield).
Rf: hexane/EtOAc (2/1) (silica chromagel; 60F$_{254}$ available from Merck): 0.3 $^1$H NMR (CDCl$_3$): δ 1.3–2.0 (m, 9H, CH$_2$ of THP and CH$_3$), 3.4–3.9 (m, 2H, OCH$_2$ THP), 4.4–4.5 (m, 2H, OCH$_2$), 5.1–5.15 (m, 1H, O—CH—O THP), 7.4–8.2 (m, 4H, H$_{arom}$), 8.9 (m, 1H, NH)

Synthesis of 2-[{N-(Tetrahydropyranyloxy)amino} sulfonyl]benzoic acid (6)

A solution of (5) above (8.70 g, 26.4 mmol) in dioxane (82 ml) was saponified by the addition of 6 M NaOH (128 ml) and water (70 ml) and the mixture heated under reflux for 2 hours. The reaction mixture was cooled (<10° C.) and then extracted with EtOAc (2×70 ml).

The combined EtOAc extracts were washed with water (135 ml), and the washing was added to the original aqueous solution. The aqueous solution was overlaid with EtOAc (400 ml) and acidified with 6 N HCl (135 ml). The phases were separated, and the aqueous phase was again extracted with EtOAc (135 ml). The combined extracts were washed with water (2×270 ml), dried (MgSO$_4$), and the solution reduced to a small volume. The precipitate which formed was filtered and then dried under vacuum to give 3.03 g of compound (6) as a white powder (49% yield after taking into account the 1.90 g of recovered starting material).

$^1$H NMR (CDCl$_3$): δ 1.4–1.8 (m, 6H, CH$_2$ of THP), 3.5–3.9 (m, 2H, OCH$_2$ THP), 5.1 (m, 1H, O—CH—O THP), 7.6–7.8 (m, 2H, H$_{arom}$), 7.9–7.95 (m, 1H, H$_{arom}$), 8.05–8.1 (m, 1H, H$_{arom}$), 9.1 (s, 1H, NH)

Synthesis of 2-(Tetrahydropyranyloxy)-1,2-benzisothiazol-3(2H)-one 1,1-Dioxide [N-(Tetrahydropyranyloxy)saccharin (7)

A stirred solution of (6) (2.87 g, 9.50 mmol) in dry distilled tetrahydrofuran (40 ml), under nitrogen, was cooled to about −10 to −15° C. in an ethanol-dry ice bath, and isobutyl chloroformate (1.70 ml, 13.10 mmol) was added followed by triethylamine (1.85 ml, 13.30 mmol). After 5 minutes the dry ice bath was removed, and when room temperature was reached, the precipitate of triethylamine hydrochloride was collected by filtration and the filtrate evaporated to give 2.67 g of a clear yellow powder. The product was recrystallised from EtOAc (18 ml) to give 2.00 g of (7) as white crystals (78% yield).

$^1$H NMR (CDCl$_3$): δ 1.6–2.2 (m, 6H, CH$_2$ of THP and CH$_3$), 3.8–4.2 (m, 2H, CH$_2$—O THP), 5.45 (s, 1H, O—CH—O THP), 7.9–8.1 (m, 4H, H$_{arom}$) $^{13}$C NMR (CDCl$_3$): δ 17.7, 24.8, 27.7, (CH$_2$ THP), 62.4 (O—CH$_2$), 104.9 (O—CH—O), 121.6, 125.5, 125.8, 134.8, 135.5, 136.4 (6C$_{arom}$), 158.5 (C═O)

Synthesis of 2-Hydroxy-1,2-benzisothaizol-3(2H)-one 1,1-Dioxide (N-Hydroxysaccharin, 8)

Compound (7) prepared as above (1.90 g, 6.70 mmol) was dissolved in tetrahydrofuran (14 ml) by warming in a water bath at 45° C., then water (3.5 ml) was added, followed by trifluoroacetic acid (0.1 ml). The solution was stirred at 45–50° C. for 7.5 h, and after the addition of water (7 ml), the mixture was evaporated to a small volume. The resulting solid suspension was collected and washed with water and then recrystallised with cold diethyl ether. After air-drying the solid was recrystallised from EtOAc/hexane to give 980 mg of crystalline (8) (73% yield).

$^1$H NMR (DMSO): δ 7.9–8.1 (m, 4H, H$_{arom}$), 11.2 (b, 1H, NOH) $^{13}$C NMR (DMSO): δ 121.5, 125.1, 125.8, 134.7, 135.2, 135.7 (6 C$_{arom}$), 157.5 (C═O)

EXAMPLE 2

Oxidation of an alkane in the presence of N-hydroxysaccharin

EXAMPLE 2A1

To 7.5 ml of acetic acid were added 504 mg (3.0 mmol) of cyclododecane and 60 mg (0.3 mmol) of N-hydroxysaccharin. The resultant mixture was stirred under an oxygen atmosphere at a temperature of 100° C. for 8 hours. The reaction was repeated several times and the products of each reaction mixture analysed by gas chromatography. The results were averaged and showed cyclododecane was transformed with an average conversion of between 19.7% to 34.4%, into cyclododecanone (average selectivity from 56.7% to 80.8%) and cyclododecanol (average selectivity of 26.1%).

EXAMPLE 2A2

To 7.5 ml of acetic acid were added 504 mg (3.0 mmol) of cyclododecane and 60 mg (0.3 mmol) of N-hydroxysaccharin. The resultant mixture was stirred under an oxygen atmosphere at a temperature of 100° C. for 24 hours. The reaction was repeated several times and the products of each reaction mixture analysed by gas chromatography. The results were averaged and showed cyclododecane was transformed with an average conversion of between 50.0% to 69.8%, into cyclododecanone (average selectivity between 31.9% to 52.0%) and cyclododecanol (average selectivity of 1.2%).

EXAMPLE 3

Comparison of the Efficiency of N-hydroxysaccharin and N-hydroxyphthalimide (of EP-A-824,962) at various temperatures

EXAMPLES 3A1–3A3

To 7.5 ml of acetic acid were added 504 mg (3.0 mmol) of cyclododecane, 60 mg (0.3 mmol) of N-hydroxysaccharin and 3.9 mg (0.015 mmol) of acetylacetonatocobalt Co(acac)$_2$. The resultant mixture was stirred under an oxygen atmosphere at a temperature of either 100° C./75° C./50° C. for the period of time indicated in Table 1 below. Each reaction mixture was then analysed by gas chromatography to determine the percentage conversion of cyclododecane and the reaction selectivity for the products, cyclododecanone and cyclododecanol. The results are set out in Table 1 below.

EXAMPLES 3A4–3A6

To 7.5 ml of acetic acid were added 504 mg (3.0 mmol) of cyclododecane, 48.9 mg (0.3 mmol) of N-hydroxyphthalimide (referred to herein for simplicity and brevity as "NHPI") and 3.9 mg (0.015 mmol) of acetylacetonatocobalt Co(acac)$_2$. The resultant mixture was stirred under an oxygen atmosphere at a temperature of either 100° C./75° C./50° C. for the time period indicated in Table 1 below. Each reaction mixture was analysed as described above and the results set out in Table 1.

TABLE 1

| Example | Catalyst | Temperature/ Reaction Time | Conversion | Selectivity for C$_1$ | Selectivity for C$_2$ | C$_1$ + C$_2$ |
|---|---|---|---|---|---|---|
| 3A1 |  | 100° C., 6 h | 64% | 31% | 5.5% | 36.5% |
| 3A2 | NHS | 75° C., 8 h | 43% | 45% | 12% | 57% |
| 3A3 |  | 50° C., 24 h | 41.5% | 46.5% | 12.5% | 59% |
| 3A4 |  | 100° C., 4 h | 57% | 29% | 7% | 36% |
| 3A5 | NHPI | 75° C., 8 h | 36% | 42% | 8% | 50% |
| 3A6 |  | 50° C., 24 h | 0% | / | / | / |

TABLE 1-continued

| Example | Catalyst | Temperature/ Reaction Time | Conversion | Selectivity for $C_1$ | Selectivity for $C_2$ | $C_1 + C_2$ |
|---------|----------|----------------------------|------------|------------------------|------------------------|-------------|

$C_1$ is cyclododecanone
$C_2$ is cyclododecanol

As is demonstrated in Example 3 above, the conversion of cyclododecane in the presence of the N-hydroxysaccharin catalyst is higher than in the presence of N-hydroxyphthalimide (of EP-A-824,962) at 100° C. and 75° C., being respectively 64% and 57% at 100° C., and 43% and 36% at 75° C. When the oxidation reaction is carried out in the presence of N-hydroxyphthalimide at 50° C., the reaction was found not to proceed. Conversely, a 41.5% conversion of cyclododecane was observed when the reaction was performed in the presence of N-hydroxysaccharin.

EXAMPLE 4

Oxidation of an alkane in the presence of N-hydroxysaccharin and a co-catalyst

Examples 4A1 to 4A4 demonstrate the influence of temperature on reaction conversion and selectivity, employing Co(acac)$_2$ (acetylacetonatocobalt) as the co-catalyst.

Examples 4A5 to 4A7 demonstrate the variation in conversion and selectivity when Co(OAc)$_2$.4H$_2$O is employed as the co-catalyst instead of Co(acac)$_2$.

The results are shown in Table 2 below.

TABLE 2

| Example | T (° C.) | Time (h) | Conv. (%) | $C_1$ (%) | $C_2$ (%) | $C_3$ (%) | $C_1 + C_2 + C_3$ (%) |
|---------|----------|----------|-----------|-----------|-----------|-----------|------------------------|
| 4A1 | 100 | 6 | 64 | 31 | 5.5 | 2 | 38.5 |
| 4A2 | 75 | 8 | 43 | 45 | 12 | 2 | 59 |
| 4A3 | 60 | 10 | 35 | 43 | 12.5 | 1 | 56.5 |
| 4A4 | 50 | 20 | 41.5 | 46.5 | 12.5 | 2 | 61 |
| 4A5 | 100 | 6 | 63.5 | 32.5 | 5 | 2.5 | 40 |
| 4A6 | 75 | 8 | 50 | 42.5 | 9 | 2 | 53.5 |
| 4A7 | 50 | 24 | 45 | 52 | 11 | 2 | 65 |

$C_1$ is cyclododecanone
$C_2$ is cyclododecanol
$C_3$ is cyclododecyl acetate

EXAMPLE 4A1

To 7.5 ml of acetic acid were added 504 mg (3.0 mmol) of cyclododecane, 60 mg (0.3 mmol) of N-hydroxysaccharin and 3.9 mg (0.015 mmol) of acetylacetonatocobalt Co(acac)$_2$. The resultant mixture was stirred under an oxygen atmosphere at a temperature of 100° C. for 6 hours. The products in the reaction mixture were analysed by gas chromatography, and according to this analysis, cyclododecane was transformed, with a conversion of 64%, into cyclododecanone (selectivity 31%, yield 20%) and cyclododecanol (selectivity 5.5%, yield 3.5%) and cyclododecyl acetate (selectivity 2%, yield 1.5%).

EXAMPLE 4A2

The reaction was conducted in generally the same manner as described in Example 4A1, except the reaction was carried out at 75° C. for 8 hours instead of 100° C. for 6 hours. GC analysis of the reaction mixture showed that cyclododecane was transformed, with a conversion of 43%, into cyclododecanone (selectivity 45%, yield 19.5%), cyclododecanol (selectivity 12%, yield 5%) and cyclododecyl acetate (selectivity 2%, yield 1%).

EXAMPLE 4A3

The reaction was conducted in generally the same manner as described in Example 4A1, except the reaction was carried out at 60° C. for 10 hours instead of 100° C. for 6 hours. GC analysis of the reaction mixture showed that cyclododecane was transformed, with a conversion of 35%, into cyclododecanone (selectivity 43%, yield 15%), cyclododecanol (selectivity 12.5%, yield 4.5%) and cyclododecyl acetate (selectivity 1%, yield 0.5%).

EXAMPLE 4A4

The reaction was conducted in generally the same manner as described in Example 4A1, except the reaction was carried out at 50° C. for 20 hours instead of 100° C. for 6 hours. GC analysis of the reaction mixture showed that cyclododecane was transformed, with a conversion of 41.5%, into cyclododecanone (selectivity 46.5%, yield 19.5%), cyclododecanol (selectivity 12.5%, yield 5%) and cyclododecyl acetate (selectivity 2%, yield 1%).

EXAMPLE 4A5

The reaction was conducted in generally the same manner as described in Example 4A1 using 3.7 mg (0.015 mmol) of Co(OAc)$_2$.4H$_2$O instead of Co(acac)$_2$. GC analysis of the reaction mixture showed that cyclododecane was transformed, with a conversion of 63.5%, into cyclododecanone (selectivity 32.5%, yield 20.5%), cyclododecanol (selectivity 5%, yield 3%) and cyclododecyl acetate (selectivity 2.5%, yield 1.5%).

EXAMPLE 4A6

The reaction was conducted in generally the same manner as described in Example 4A1 using 3.7 mg (0.015 mmol) of Co(OAc)$_2$.4H$_2$O instead of Co(acac)$_2$ and was carried out at 75° C. for 8 hours instead of 100° C. for 6 hours. GC analysis of the reaction mixture showed that cyclododecane was transformed, with a conversion of 50%, into cyclododecanone (selectivity 42.5%, yield 21.5%), cyclododecanol (selectivity 9%, yield 4.5%) and cyclododecyl acetate (selectivity 2%, yield 1%).

EXAMPLE 4A7

The reaction was conducted in generally the same manner as described in Example 4A1 using 3.7 mg (0.015 mmol) of Co(OAc)$_2$.4H$_2$O as the co-catalyst and the reaction carried out at 50° C. for 24 hours. GC analysis of the reaction mixture showed that cyclododecane was transformed, with a conversion of 45%, into cyclododecanone (selectivity 52%, yield 23.5%), cyclododecanol (selectivity 11%, yield 5%) and cyclododecanol acetate (selectivity 2%, yield 1%).

Examples 4A8 to 4A17 demonstrate the conversion and selectivities obtained when cyclododecane is oxidised in the presence of N-hydroxysaccharin and different metal co-catalysts. The results are shown in Table 3 below.

TABLE 3

| Example | T (° C.) | Time (h) | Co-catalyst | Conv (%) | $C_1$ (%) | $C_2$ (%) | $C_3$ (%) | $C_1 + C_2 + C_3$ (%) |
|---|---|---|---|---|---|---|---|---|
| 4A8  | 100 | 8  | Cu(OAc)$_2$.4H$_2$O     | 55   | 32   | 6    | 3   | 41   |
| 4A9  | 75  | 10 | Cu(OAc)$_2$.4H$_2$O     | 28   | 34   | 18   | 6.5 | 58.5 |
| 4A10 | 100 | 6  | Cu(acac)$_2$            | 44.5 | 31   | 11.5 | 2   | 44.5 |
| 4A11 | 100 | 2  | Ru(CH$_3$CN)$_4$Cl$_2$  | 21   | 31.5 | 15   | 10  | 56.5 |
| 4A12 | 75  | 2  | Ru(CH$_3$CN)$_4$Cl$_2$  | 24   | 35.5 | 14.5 | 8.5 | 58.5 |
| 4A13 | 100 | 6  | Fe(acac)$_3$            | 31   | 32.5 | 23.5 | 2   | 58   |
| 4A14 | 75  | 20 | Fe(acac)$_3$            | 23.5 | 37.5 | 32.5 | 2.5 | 72.5 |
| 4A15 | 100 | 5  | Co(acac)$_3$            | 64   | 30   | 6    | 3   | 39   |
| 4A16 | 60  | 24 | Co(acac)$_3$            | 35.5 | 43   | 19   | 2   | 64   |
| 4A17 | 50  | 24 | Co(acac)$_3$            | 22   | 48   | 26   | 2.5 | 76.5 |

$C_1$ is cyclododecanone
$C_2$ is cyclododecanol
$C_3$ is cyclododecyl acetate

EXAMPLE 4A8

The reaction was conducted in generally the same manner as Example 4A1 using 2.9 mg (0.015 mmol) of Cu(OAc)$_2$.4H$_2$O instead of Co(acac)$_2$, and cyclododecane was transformed, with a conversion of 55%, into cyclododecanone (selectivity 32%, yield 17.5%), cyclododecanol (selectivity 6%, yield 3.5%) and cyclododecyl acetate (selectivity 3%, yield 1.5%).

EXAMPLE 4A9

The reaction was conducted in generally the same manner as Example 4A1 using 2.9 mg (0.015 mmol) of Cu(OAc)$_2$.4H$_2$O as the co-catalyst and the reaction carried out at 75° C. for 10 hours. GC analysis of the reaction mixture showed that cyclododecane was transformed, with a conversion of 28%, into cyclododecanone (selectivity 34%, yield 9.5%), cyclododecanol (selectivity 18%, yield 5%) and cyclododecyl acetate (selectivity 6.5%, yield 2%).

EXAMPLE 4A10

The reaction was conducted in generally the same manner as Example 4A1 using 4.0 mg (0.015 mmol) of Cu(acac)$_2$ instead of Co(acac)$_2$, and cyclododecane was transformed, with a conversion of 44.5%, into cyclododecanone (selectivity 31%, yield 14%), cyclododecanol (selectivity 11.5%, yield 5%) and cyclododecyl acetate (selectivity 2%, yield 1%).

EXAMPLE 4A11

The reaction was conducted in generally the same manner as Example 4A1 using 4.0 mg (0.015 mmol) of Ru(CH$_3$CN)$_4$ Cl$_2$ instead of Co(acac)$_2$. After 2 hours, no further conversion was observed and the reaction was stopped. GC analysis of the reaction mixture showed that cyclododecane was transformed, with a conversion of 21%, into cyclododecanone (selectivity 31.5%, yield 6.5%), cyclododecanol (selectivity 15%, yield 3%) and cyclododecyl acetate (selectivity 10%, yield 2%).

EXAMPLE 4A12

The reaction was conducted in generally the same manner as Example 4A1 using 4.0 mg (0.015 mmol) of Ru(CH$_3$CN)$_4$ Cl$_2$ at 75° C. for 2 hours, instead of Co(acac)$_2$ at 100° C. for 6 hours. After 2 hours, no further conversion was observed and the reaction was stopped. GC analysis of the reaction mixture showed that cyclododecane was transformed under these conditions, with a conversion of 24%, into cyclododecanone (selectivity 35.5%, yield 8.5%), cyclododecanol (selectivity 14.5%, yield 3.5%) and cyclododecyl acetate (selectivity 8.5%, yield 2%).

EXAMPLE 4A13

The reaction was conducted in generally the same manner as Example 4A1 using 5.3 mg (0.015 mmol) of Fe(acac)$_3$ instead of Co(acac)$_2$, and cyclododecane was transformed, with a conversion of 31%, into cyclododecanone (selectivity 32.5%, yield 10%), cyclododecanol (selectivity 23.5%, yield 7.5%) and cyclododecyl acetate (selectivity 2%, yield 0.5%).

EXAMPLE 4A14

The reaction was conducted in generally the same manner as Example 4A1 using 5.3 mg (0.015 mmol) of Fe(acac)$_3$ as the co-catalyst and the reaction carried out at 75° C. for 20 hours. GC analysis of the reaction mixture showed cyclododecane was transformed, with a conversion of 23.5%, into cyclododecanone (selectivity 37.5%, yield 9%), cyclododecanol (selectivity 32.5%, yield 7.5%) and cyclododecyl acetate (selectivity 2.5%, yield 0.5%).

EXAMPLE 4A15

The reaction was conducted in generally the same manner as Example 4A1 using 5.3 mg (0.015 mmol) of Co(acac)$_3$ instead of Co(acac)$_2$, and cyclododecane was transformed, with a conversion of 64%, into cyclododecanone (selectivity 30%, yield 19.5%), cyclododecanol (selectivity 6%, yield 4%) and cyclododecyl acetate (selectivity 3%, yield 2%).

EXAMPLE 4A16

The reaction was conducted in generally the same manner as Example 4A1 using 5.3 mg (0.015 mmol) of Co(acac)$_3$ as the co-catalyst and the reaction carried out at 60° C. for 24 hours. GC analysis of the reaction mixture showed that cyclododecane was transformed, with a conversion of 35.5%, into cyclododecanone (selectivity 43%, yield 15.5%), cyclododecanol (selectivity 19%, yield 7%), cyclododecyl acetate (selectivity 2%, yield 0.5%) and dodecanediacid (selectively 18.5%, yield 4%).

EXAMPLE 4A17

The reaction was conducted in generally the same manner as Example 4A1 using 5.3 mg (0.015 mmol) of Co(acac)$_3$ as the co-catalyst and the reaction carried out at 50° C. for 24 hours. GC analysis of the reaction mixture showed that cyclododecane was transformed, with a conversion of 22%, into cyclododecanone (selectivity 48%, yield 11%), cyclododecanol (selectivity 26%, yield 5.5%), cyclododecyl acetate (selectivity 2.5%, yield 0.5%) and dodecanediacid (selectivity 18.5%, yield 4%).

The results demonstrate that by utilising a co-catalyst comprising the element copper (see Examples 4A8 to 4A10) instead of the cobalt (II) complex of Examples 4A1 to 4A7, the resulting conversions are lower, but the selectivities are comparable to, or slightly better than those obtained utilising the cobalt (II) complex. When the oxidation reaction is carried out in the presence of Fe(acac)$_3$ a moderate conversion of cyclododecane is realised, with good selectivity toward the formation of the oxidation reaction products at both 100° C. and 75° C. Further, from the results presented in Table 3, at 100° C., the conversions and selectivities obtained in the presence of a cobalt (III) complex (Co(acac)$_3$) are similar to those obtained with cobalt (II) complexes. At lower temperatures, cobalt (III) leads to lower conversions than cobalt (II), together with a higher selectivity towards the formation of cyclododecanone, cyclododecanol and cyclododecyl acetate.

EXAMPLES 5A1 TO 5A2

Examples 5A1 to 5A9 demonstrate the reaction conversion and selectivities obtained in different solvents.

The results are shown in Table 4 below.

TABLE 4

| Example | Solvent | T(° C.) | Co-catalyst | Time (h) | Conv (%) | $C_1$ (%) | $C_2$ (%) | $C_4$ (%) | Total (%) |
|---|---|---|---|---|---|---|---|---|---|
| 5A1 | CH$_3$CN | 85° C. | Co(acac)$_2$ | 22 | 28 | 34.5 | 14 | nd. | 48.5 |
| 5A2 | PhCl | 100° C. | Co(acac)$_2$ | 8 | 24 | 52.5 | 26.5 | nd. | 79 |
| 5A3 | PhCF$_3$ | 100° C. | Co(acac)$_2$ | 24 | 32 | 54 | 20 | nd. | 74 |
| 5A4 | PhCF$_3$ | 80° C. | Co(acac)$_2$ | 48 | 24 | 58 | 21 | nd. | 79 |
| 5A5 | PhCF$_3$ | 100° C. | Co(acac)$_3$ | 4 | 34.5 | 64 | 16.5 | 5 | 85.5 |
| 5A6 | PhCF$_3$ | 80° C. | Co(acac)$_3$ | 10 | 24 | 72 | 17.5 | 0 | 89.5 |
| 5A7 | PhCF$_3$ | 100° C. | Co(OAc)$_2$ | 24 | 26 | 49 | 30 | nd. | 79 |
| 5A8 | PhCF$_3$ | 100° C. | Cu(acac)$_2$ | 8 | 31.5 | 60.5 | 9.5 | nd. | 70 |
| 5A9 | PhCF$_3$ | 100° C. | Fe(acac)$_3$ | 8 | 20 | 58.5 | 37 | nd. | 95.5 |

$C_1$ is cyclododecanone
$C_2$ is cyclododecanol
$C_4$ is dodecanediacid
Total = $C_1$ + $C_2$ + $C_4$
nd. is not determined

EXAMPLE 5A1

To 7.5 ml of acetonitrile were added 504 mg (3.0 mmol) of cyclododecane, 60 mg (0.3 mmol) of N-hydroxysaccharin and 3.9 mg (0.015 mmol) of acetylacetonatocobalt Co(acac)$_2$. The resultant mixture was stirred under an oxygen atmosphere at a temperature of 85° C. for 22 hours. The products in the reaction mixture were analysed by gas chromatography, with cyclododecane being transformed, with a conversion of 28%, into cyclododecanone (selectivity 34.5%, yield 9.5%) and cyclododecanol (selectivity 14%, yield 4%).

EXAMPLE 5A2

The reaction procedure was generally as described in Example 5A1, except the reaction was carried out at 100° C. in chlorobenzene for 8 hours. Under these conditions cyclododecane was transformed, with a conversion of 24%, into cyclododecanone (selectivity 52.5%, yield 12.5%) and cyclododecanol (selectivity 26.5%, yield 6.5%).

EXAMPLE 5A3

The reaction procedure was generally as described in Example 5A1, except the reaction was carried out at 100° C. in trifluorotoluene (9 ml) for 24 hours. Under these conditions cyclododecane was transformed, with a conversion of 32%, into cyclododecanone (selectivity 54%, yield 17.5%) and cyclododecanol (selectivity 20%, yield 6.5%).

EXAMPLE 5A4

The reaction procedure was generally as described Example 5A1, except the reaction was carried out at 80° C. in trifluorotoluene (9 ml) for 48 hours. Cyclododecane was transformed under these conditions with a conversion of 24%, into cyclododecanone (selectivity 58%, yield 14%) and cyclododecanol (selectivity 21%, yield 5%).

EXAMPLE 5A5

To 9 ml of trifluorotoluene was added 504 mg (3.0 mmol) of cyclododecane, 60 mg (0.3 (mmol) of N-hydroxysaccharin and 5.3 mg (0.015 mmol) of acetylacetonatocobalt Co(acac)$_3$. The resultant mixture was stirred under an oxygen atmosphere at a temperature of 100° C. for 4 hours. The products in the reaction mixture were analysed by gas chromatography, with cyclododecane being transformed, with a conversion of 34.5%, into cyclododecanone (selectivity 64%, yield 22%), cyclododecanol (selectivity 16.5%, yield 5.5%) and dodecanediacid (selectivity 5%, yield 2%).

EXAMPLE 5A6

The reaction procedure was generally as described in Example 5A5, except the reaction was carried out at 80° C. for 10 hours instead of 100° C. for 4 hours. Cyclododecane was transformed under these conditions with a conversion of 24%, into cyclododecanone (selectivity 72%, yield 17.5%) and cyclododecanol (selectivity 17.5%, yield 4%).

EXAMPLE 5A7

The reaction procedure was generally as described in Example 5A3 using 3.7 mg (0.015 mmol) of Co(OAc)$_2$. 4H$_2$O instead of Co(acac)$_2$. Under these reaction conditions, cyclododecane was transformed with a conversion of 26% under these conditions into cyclododecanone (selectivity 49%, yield 13%) and cyclododecanol (selectivity 30%, yield 8%).

EXAMPLE 5A8

The reaction was conducted in the same manner as Example 5A3 using 3.9 mg (0.015 mmol) of Cu(acac)$_2$ instead of Co(acac)$_2$. Cyclododecane was transformed after 8 hours of reaction, with a conversion of 31.5%, into cyclododecanone (selectivity 60.5%, yield 19%) and cyclododecanol (selectivity 9.5%, yield 3%).

EXAMPLE 5A9

The reaction was conducted in the same manner as Example 5A3 using 5.3 mg (0.015 mmol) of Fe(acac)$_3$ instead of Co(acac)$_2$. Cyclododecane was transformed after 8 hours of reaction, with a conversion of 20%, into cyclododecanone (selectivity 58.5%, yield 11.5%) and cyclododecanol (selectivity 37%, yield 7.5%).

The results demonstrate that trifluorotoluene is an effective solvent for the oxidation reaction.

EXAMPLES 6A1 TO 6A8

Examples 6A1 to 6A8 demonstrate the conversion and selectivities obtained when cyclooctane is oxidised in the presence of N-hydroxysaccharin and different metal co-catalysts. The results are shown in Table 5 below.

TABLE 5

| Example | T (°C.) | Time (h) | Co-catalyst | Conv (%) | $C_5$ (%) | $C_6$ (%) | $C_7$ (%) | $C_8$ (%) | Total (%) |
|---|---|---|---|---|---|---|---|---|---|
| 6A1 | 100 | 6 | Co(acac)$_2$ | 88 | 42 | 3 | 11.5 | 18 | 74.5 |
| 6A2 | 50 | 9 | Co(acac)$_2$ | 34 | 48.5 | 24.5 | 4.5 | 19 | 96.5 |
| 6A3 | 50 | 8 | Co(OAc)$_2$.4H$_2$O | 43.5 | 43.5 | 18 | 4.5 | 23 | 89 |
| 6A4 | 75 | 24 | Fe(acac)$_3$ | 56 | 33.5 | 16 | 7 | 21 | 77.5 |
| 6A5 | 60 | 24 | Co(acac)$_3$ | 77.5 | 44 | 6.5 | 7 | 21 | 78.5 |
| 6A6 | 50 | 24 | Co(acac)$_3$ | 53 | 17.5 | 16 | 1 | 20.5 | 55 |
| 6A7 | 100 | 1.5 | Co(acac)$_3$ | 30 | 54.5 | 22 | 0 | 22 | 98.5 |
| 6A8 | 80 | 8 | Co(acac)$_3$ | 40 | 45 | 10.5 | 0 | 19 | 74.5 |

$C_5$ is cyclooctanone
$C_6$ is cyclooctanol
$C_7$ is 1,4-cyclooctanedione
$C_8$ is octanediacid
Total = $C_5 + C_6 + C_7 + C_8$

EXAMPLE 6A1

To 7.5 ml of acetic acid were added 336 mg (3.0 mmol) of cyclooctane, 60 mg (0.3 mmol) of N-hydroxysaccharin and 3.9 mg (0.015 mmol) of acetylacetonatocobalt Co(acac)$_2$. The resultant mixture was stirred under an oxygen atmosphere at a temperature of 100° C. for 6 hours. The products in the reaction mixture were analysed by gas chromatography, with cyclooctane being transformed, with a conversion of 88%, into cyclooctanone (selectivity 42%, yield 37%), cyclooctanol (selectivity 3%, yield 2.5%), 1,4-cyclooctanedione (selectivity 11.5%, yield 10%) and octanediacid (selectivity 18%, yield 16%).

EXAMPLE 6A2

The reaction procedure was generally as described in Example 6A1, except the reaction was carried out at 50° C. for 9 hours instead of 100° C. for 6 hours. Cyclooctane was transformed under these conditions, with a conversion of 34%, into cyclooctanone (selectivity 48.5%, yield 16.5%), cyclooctanol (selectivity 24.5%, yield 8.5%), 1,4-cyclooctanedione (selectivity 4.5%, yield 1.5%) and octanediacid (selectivity 19%, yield 6.5%).

EXAMPLE 6A3

To 27.5 ml of acetic acid were added to 336 mg (3.0 mmol) of cyclooctane, 60 mg (0.3 mmol) of N-hydroxysaccharin and 3.7 mg (0.015 mmol) of Co(OAc)$_2$.4H$_2$O. The resultant mixture was stirred under an oxygen atmosphere at a temperature of 50° C. for 9 hours. The products in the reaction mixture were analysed by gas chromatography, with cyclooctane being transformed, with a conversion of 43.5%, into cyclooctanone (selectivity 43.5%, yield 19%), cyclooctanol (selectivity 18%, yield 8%), 1,4-cyclooctanedione (selectivity 4.5%, yield 2%) and octanediacid (selectivity 23%, yield 10%).

EXAMPLE 6A4

To 7.5 ml of acetic acid were added to 336 mg (3.0 mmol) of cyclooctane, 60 mg (0.3 mmol) of N-hydroxysaccharin and 5.3 mg (0.015 mmol) of Fe(acac)$_3$. The resultant mixture was stirred under an oxygen atmosphere at a temperature of 75° C. for 24 hours. The products in the reaction mixture were analysed by gas chromatography, with cyclooctane being transformed, with a conversion of 56%, into cyclooctanone (selectivity 33.5%, yield 19%), cyclooctanol (selectivity 16%, yield 9%), 1,4-cyclooctanedione (selectivity 7%, yield 4%) and octanediacid (selectivity 21%, yield 12%).

EXAMPLE 6A5

To 7.5 ml of acetic acid were added 336 mg (3.0 mmol) of cyclooctane, 60 mg (0.3 mmol) of N-hydroxysaccharin and 5.3 mg (0.015 mmol) of Co(acac)$_3$. The resultant mixture was stirred under an oxygen atmosphere at a temperature of 60° C. for 24 hours. The products in the reaction mixture were analysed by gas chromatography, with cyclooctane being transformed, with a conversion of 77.5%, into cyclooctanone (selectivity 44%, yield 34%), cyclooctanol (selectivity 6.5%, yield 5%), 1,4-cyclooctanedione (selectivity 7%, yield 5.5%) and octanediacid (selectivity 21%, yield 16%).

EXAMPLE 6A6

To 7.5 ml of acetic acid were added 336 mg (3.0 mmol) of cyclooctane, 60 mg (0.3 mmol) of N-hydroxysaccharin and 5.3 mg (0.015 mmol) of Co(acac)$_3$. The resultant mixture was stirred under an oxygen atmosphere at a temperature of 50° C. for 24 hours. The products in the reaction mixture were analysed by gas chromatography, with cyclooctane being transformed, with a conversion of 53%, into cyclooctanone (selectivity 17.5%, yield 9.5%), cyclooctanol (selectivity 16%, yield 8.5%), 1,4-cyclooctanedione (selectivity 1%, yield 0.5%) and octanediacid (selectivity 20.5%, yield 11%).

EXAMPLE 6A7

To 9 ml of trifluorotoluene was added 336 mg (3.0 mmol) of cyclooctane, 60 mg (0.3 mmol) of N-hydroxysaccharin and 5.3 mg (0.015 mmol) of acetylacetonatocobalt Co(acac)$_3$. The resultant mixture was stirred under an oxygen atmosphere at a temperature of 100° C. for 1.5 hours. The products in the reaction mixture were analysed by gas chromatography, with cyclooctane being transformed, with a conversion of 30%, into cyclooctanone (selectivity 54.5%, yield 16.5%), cyclooctanol (selectivity 22%, yield 6.5%) and octanediacid (selectivity 22%, yield 6.5%).

EXAMPLE 6A8

The reaction was conducted in the same manner as Example 6A7, except the reaction was carried out at 80° C. for 8 hours instead of at 100° C. for 1.5 hours. Under these conditions cyclooctane was transformed, with a conversion of 40%, into cyclooctanone (selectivity 45%, yield 18%), cyclooctanol (selectivity 10.5%, yield 4%) and octanediacid (selectivity 19%, yield 7.5%).

The invention claimed is:

1. A process for the catalytic oxidation of an alkane, which comprises contacting the alkane with a source of oxygen in the presence of a catalyst comprising a compound of the following formula:

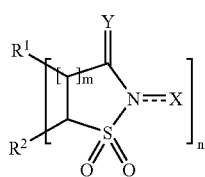

Formula 2 wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring; Y represents an oxygen atom or a sulfur atom; X represents an oxygen atom or a hydroxyl group; m denotes an integer of 0 to 4; and n denotes an integer of 1 to 3.

2. A process according to claim 1, wherein $R^1$ and $R^2$ together form an aromatic or non-aromatic ring and m=1 or 2.

3. A process according to claim 1, wherein $R^1$ and $R^2$ together form an aromatic or non-aromatic ring and m=1.

4. A process according to claim 1, wherein $R^1$ and $R^2$ together form an aromatic C6 membered ring and m=1.

5. A process according to claim 1, wherein n=1.

6. A process according to claim 1, wherein Y is an oxygen atom and X is a hydroxyl group.

7. A process according to claim 1, wherein Y is an oxygen atom.

8. A process according to claim 7, wherein m is 1.

9. A process according to claim 1, wherein $R^1$ and $R^2$ together form an aromatic ring.

10. A process according to claim 9, wherein $R^1$ and $R^2$ together form an aromatic C6 membered ring.

11. A process according to claim 1 or 7, wherein X is a hydroxyl group.

12. A process according to claim 1 or 7, wherein n is 1.

13. A process according to claim 1, wherein the catalyst is N-hydroxysaccharin.

14. A process according to claim 1, wherein the alkane is a cycloalkane.

15. A process according to claim 14, wherein the cycloalkane is a C5 to C20 membered ring.

16. A process according to claim 1, wherein the alkane is a linear alkane, benzylic alkane or allylic alkane.

17. A process according to claim 1, wherein the catalytic oxidation reaction is carried out at a temperature in the range from 20° C. to 100° C.

18. A process according to claim 1, wherein the catalyst additionally comprises a co-catalyst or mixtures thereof.

* * * * *